(12) United States Patent
Ryu et al.

(10) Patent No.: US 7,998,719 B2
(45) Date of Patent: Aug. 16, 2011

(54) CRYSTAL OF A PHOSPHATASE OF REGENERATING LIVER 1 (PRL-1) POLYPEPTIDE AND METHOD OF CRYSTALLIZATION THEREOF

(75) Inventors: Seong Eon Ryu, Taejeon-si (KR); Dae Gwin Jeong, Taejeon-si (KR); Seung-Jun Kim, Taejeon-si (KR); Jae Hoon Kim, Jeju-si (KR); Jeong Hee Son, Taejeon-si (KR)

(73) Assignee: Korea Research Institute of Bioscience and Biotechnology, Taejeon-Si (KR)

( * ) Notice: Subject to any disclaimer, the term of this patent is extended or adjusted under 35 U.S.C. 154(b) by 1073 days.

(21) Appl. No.: 11/587,404

(22) PCT Filed: Apr. 26, 2005

(86) PCT No.: PCT/KR2005/001202
§ 371 (c)(1), (2), (4) Date: Oct. 24, 2006

(87) PCT Pub. No.: WO2005/103242
PCT Pub. Date: Nov. 3, 2005

(65) Prior Publication Data
US 2009/0117580 A1 May 7, 2009

(30) Foreign Application Priority Data
Apr. 26, 2004 (KR) .................. 10-2004-0028774

(51) Int. Cl.
*C12N 9/16* (2006.01)
(52) U.S. Cl. .................................. 435/196
(58) Field of Classification Search .................. None
See application file for complete search history.

(56) References Cited

U.S. PATENT DOCUMENTS
2008/0201123 A1* 8/2008 Cosgrove .................. 703/11

OTHER PUBLICATIONS

McPherson et al., Eur. J. Biochem. 189:1-23, 1990.*
Kierzek et al., Biophys Chem 91:1-20, 2001.*
Peters et al., J. Biol. Chem. 276:13718-13726, 2001.*
Diamond et al., Mol. Cell. Biol. 14:3752-3762, 1994.*
"Amersham Protein Purification Handbook", Oct. 2001, p. 59.*
Nemeth et al., Genes Dev. 12:3059-3073, 1998.*
Streelman et al., Physiol. Genomics 9:1-4, 2002.*
Merriam-Webster Online Dictionary definition of "represent", obtained from www.merriam-webster.com, last viewed on Aug. 3, 2009.*
Sun et al., "Structure and Biochemical Properties of PRL-1, a Phosphatase Implicated in Cell Growth, Differentiation, and Tumor Invasion", Biochemistry 44:12009-12021, 2005.*
Jeong et al., "Trimeric Structure of PRL-1 Phosphatase Reveals an Active Enzyme Conformation and Regulation Mechanisms", J. Mol. Biol. 2005 345:401-413.
Kozlov et al., "Structural Insights into Molecular Function of the Metastasis-associated Phosphatase PRL-3", J. Biol. Chem. 2004 279(12):11882-11889.
Peng et al., "The Gene Encoding Human Nuclear Protein Tyrosine Phosphatase, PRL-1", J. Biol. Chem. 1998 273 (27) :17286-17295.
Zeng et al., "PRL-3 and PRL-1 Promote Cell Migration, Invasion and Metastasis", Cancer Research 2003 63:2716-2722.

* cited by examiner

*Primary Examiner* — David J Steadman
(74) *Attorney, Agent, or Firm* — Licata & Tyrrell P.C.

(57) ABSTRACT

The present invention relates to a crystal structure of PRL-1 (Phospatase of Regenerating Liver) protein and a method of crystallization thereof. It has been found that the PRL-1 protein has a tertiary structure having 5 strands of beta-sheet surrounded by 6 alpha-helices and well-arranged active site with closed P-loop, and monomers form a trimer through farnesylation site in the C-terminus of said protein. Thus intra-cellular migration and membrane localization can be achieved. The said crystal structure of PRL-1 protein of the present invention is very useful for the development the agent which inhibits carcinogenesis and metastasis of the cancer.

8 Claims, 11 Drawing Sheets
(11 of 11 Drawing Sheet(s) Filed in Color)

CRYSTAL OF A PHOSPHATASE OF REGENERATING LIVER 1 (PRL-1) POLYPEPTIDE AND METHOD OF CRYSTALLIZATION THEREOF

TECHNICAL FIELD

The present invention relates to a crystal structure of PRL-1 protein and a method of crystallization thereof, more precisely, a method of crystallization of PRL-1 protein including the steps of mass-expressing human originated PRL-1 protein in *E-coli* transformant and purifying those expressed proteins, and crystals prepared thereby. From this invention, tertiary active structure of PRL-1 protein has been confirmed.

BACKGROUND ART

Protein tyrosine phosphatases (PTPs) play an important role in intracellular signal transduction mediating cell growth, cell differentiation, transcription and metabolism (Neel, B. G. et al., Curr. Opin. Cell Biol. 9, 193-204, 1997; Zhang, Z.-Y. Annu. Rev. Pharmacol. Toxicol. 41, 209-234, 2002). Members of PTP family have been known to have a preserved active site where active cysteine residues reside. PTP family is composed of over 120 proteins, and it is divided into two sub-groups according to their target proteins and structural characteristics. The first sub-group is characterized by mediating dephosphorylation of pTyr only, and the second sub-group is characterized by mediating dephosphorylation of not only pTyr but also pSer/pThr.

Among them, phospatase of regenerating liver (referred as "PRL" hereinafter) is divided into three subtypes; PRL-1~3, and has prenylated C-terminal (Diamond, R. H. et al., Mol. Cell. Biol. 14, 3752-3762, 1994). PRL-1 is an immediate early gene which is found in mouse liver and was cloned foremost (Mohn, K. L. et al. Mol. Cell. Biol. 11, 381-390, 1991). Then, PRL-2 and PRL-3 were found by homologous sequence search. The said PRL proteins include PTP motif sequence, which does not have homology with earlier PTP protein sequences, though. The modified phenotype of epithelial cells is resulted from the over-expression of PRL-1 or PRL-2, and cells transfected with those proteins turn into tumor cells in a nude mouse (Cates, C. A. et al., Cancer Lett. 110, 49-55, 1996). PRL-3 is remarkably over-expressed during the metastasis of colorectal cancer to the liver. However, the protein is not expressed in non-metastatic cancer cells or in general colorectal epithelial cells (Saha, S. et al., Science 294, 1343-1346, 2001). Amplification of PRL-3 gene is also found in the regions of metastasis in patients with different cancers.

Pentamidine, known as a PRL protein inhibitor, definitely inhibits the growth of WM9 human melanoma in a nude mouse (Manas, M. K. et al. Mol. Cancer. Therapeutics 1, 1255-1264, 2002). The over-expressions of PRL-1 and PRL-3 are involved in metastasis by accelerating migration and infiltration of cells (Zeng, Q. et al. Cancer Research 63, 2716-2722, 2003).

PRL proteins have preserved CAAX sequence (C: cysteine, A: aliphatic amino acid, X: amino acid) at C-terminal for prenylation. Protein prenylation, helping migration of a protein to cell membrane, plays an important role in intracellular signal transduction, along with receptor complex binding Ras and G-protein (Silvius, J. R., J. Membrane Biol. 190, 83-92, 2002; Takida, S. et al., J. Biol. Chem. 278, 17284-17290, 2003). Prenylated PRL proteins are transferred to plasma membrane and early endosome. At this time, when a farnesyltransferase inhibitor is treated thereto or mutation is induced in prenylated area, the PRL proteins are biased to nucleus (Zeng, Q. et al., J. Biol. Chem. 275, 21444-21452, 2000). According to a recent report, PRL-1 is biased cell cycle dependently (Wang, J. et al., J. Biol. Chem. 277, 46659-46668, 2002). That is, in nondividing cells, PRL-1 protein is biased to ER (endoplasmic reticulum) farnesylation dependently. In the mean time, in dividing cells, PRL-1 protein is biased to centrosome and spindle fiber, suggesting that PRL-1 plays an important role in cell division procedure by regulating the growth of spindle fiber.

Although accumulated test results on the effect of PRL protein on cell proliferation and tumorigenesis provide the possibility of a PRL protein inhibitor as a promising anticancer agent, concrete intracellular mechanism of PRL protein has not been disclosed, yet. It was recently reported that PRL-3 has NMR structure (Kozlov, G. et al., J. Biol. Chem. Epub M312905200, 2004), but it is an open structure of WPD loop, meaning that residues of an active site are rearranged from their enzyme catalytic site. Thus, exactly speaking, it is not an active structure of PRL enzyme.

For the purpose of elucidating detailed mechanism of PRL enzyme on the recognition of substrate and the regulation of activity, the present inventors provide a method of crystallization of the protein including the steps of mass-expressing human originated PRL-1 protein in *E. coli* transformant and purifying the expressed proteins, and also provide the resultant protein crystals. The present inventors completed this invention by confirming the tertiary active structure of PRL-1 protein at the resolution of 2.7 Å. It was confirmed that PRL-1 protein has a tertiary structure having 5 strands of beta-sheet surrounded by 6 alpha-helices and well arranged active site with closed P-loop, and monomers form a trimer through farnesylation site in the C-terminus of the PRL-1 protein. Thus, intracellular migration and membrane localization can be achieved.

DISCLOSURE

Technical Problem

It is an object of the present invention to provide PRL-1 protein crystal which plays an important role in proliferation and metastasis of cancer, a preparation method of the crystal, and to examine PRL-1 specific tertiary active structure. It is another object of the invention to provide a method for the development of a PRL-1 protein inhibitor.

Technical Solution

To achieve the above objects, the present invention provides PRL-1 crystal having a unique tertiary active structure.

The present invention also provides a PRL-1 (C104S) protein.

The present invention further provides a preparation method for PRL-1 crystal.

The present invention also provides a screening method for a PRL-1 protein inhibitor by using PRL-1 crystal of the invention.

The present invention further provides a development method for a PRL-1 protein inhibitor by using PRL-1 crystal of the invention.

Hereinafter, the present invention is described in detail.

The present invention provides PRL-1 crystal having a unique tertiary active structure.

The present inventors have found a crystal structure of human PRL-1 protein at the resolution of 2.7 Å.

PRL-1 protein molecules inside of the crystal structure contain pockets of wide thin active area surrounded by flat surface. The pocket of the active area is covered by the conserved sequence of PRL-1 protein 'WFPDD (SEQ ID NO:10)' loop, and important enzyme-catalytic residues are well arranged therein, indicating that the crystal structure found by the inventors is an enzyme active structure. Catalytic cysteine is close to the other cysteine and the two cysteines form a disulfide bond under the oxidative condition.

The present inventors also confirmed that PRL-1 forms a trimer in the crystal. And the trimer was proved by the biochemical analysis to play an important role in biological functions of the protein. The above founding has established structural base for the development of a PRL enzyme inhibitor, and indicates that the activity of PRL-1 is regulated by intracellular oxidation/reduction and oligomerization.

Particularly, the crystal structure of PRL-1 protein of the present invention has 5 strands of β-sheet surrounded by 6 α-helices in the center (see FIG. 1). The approximate molecular size is 45×40×35 Å and one side of the beta-sheet is covered by two alpha-helices (α1 and α2) and the other side of the sheet is covered by 4 alpha-helices (α3~α6). Although PRL-1 shows low homology (30%) with other phosphatases, it has a very similar skeletal structure having double-specificity to phosphatase. Similar structures were searched by using Dali server 15. As a result, phosphatases having double-specificity, like VHR16, MKP17 and PTEN18, were found being in the Z-value range of 18.0~16.0, meaning they have a similar structure to PRL-1.

From the comparison of structures between PRL-1 and VHR, it was confirmed that 124 residues were correspondingly arranged in the range of 1.63 Å root mean square deviation, and the correspondence was greater in the center but not in other regions including loop and secondary structures (see FIG. 2). The biggest difference was that PRL-1 was deficient in N-terminal helix α0, loop α0-β1 and loop β3-α2 (see FIG. 2 and FIG. 5). Helix α0 and loop α0-β1 play an important role in the recognition of substrate in VHR and other phosphatases. Thus, without N-terminal sequence, PRL-1 recognizes another substrate, and the deficient of loop β3-α2 results in the changes of pocket entrance of an active area. Non-corresponding regions between the structures of PRL-1 and VHR were also found in loop β1-β2, β2-α1 and β4-α3 (see FIG. 2).

6 PRL-1 molecules are in asymmetric unit of PRL-1 crystal, and 3 of them form a trimer by triple symmetrical combination, and the rest 3 of them form another trimer similar to the first trimer which interacts with the first one. C-terminal tails of each molecule reside on the same side of the trimer formed by triple symmetrical binding, and farnesylation seems to be induced in CAAX motif of the tails, leading to the interaction with cell membrane. The active site is found outside of the trimer, indicating that the formation of a trimer dose not affect PRL-1 enzyme activity (see FIG. 3 and FIG. 4).

Like other PTP proteins, PRL-1 has its active region in the center of the molecule, and is composed of P-loop (His103-Cys-(X)5-Arg110 (SEQ ID NO:7), X is general amino acid) which is a preserved PTP motif (see FIG. 6), wherein numbers of amino acid residues correspond to a full length PRL-1 protein having the amino acid sequence of SEQ ID NO: 6.

WPD loop of PTP family is changed into WFPDD (SEQ ID NO: 10, $68^{th}$~$72^{nd}$ residues) in PRL-1. Aspartic acid residue in WPD loop acts as a general acid for enzyme reaction (Zhang, Z.-Y., Annu. Rev. Pharmacol. Toxicol. 41, 209-234, 2002). During the binding of substrate, WPD loop forms a closed conformation and covers active site, making leaving group be near side chain of aspartic acid. In PRL-1 structure, sulphuric acid ion is bound with an enzyme active site formed by atoms of main chain amides of P-loop and side chain of Arg-110 (see FIG. 7). The sulphuric acid ion is similar to phosphoric acid group of a substrate in properties, and WFPDD loop of PRL-1 forms closed conformation, an active structure similar to that of WPD loop of VHR16.

Comparison of active site structures has been made between PRL-1 and VHR. The second aspartic acid (Asp72) of WFPDD loop is arranged in the same site where the general acid residue of VHR is, indicating that the Asp72 acts as a general acid in PRL-1 (see FIG. 5 and FIG. 7). In accordance with earlier reports, the present inventors confirmed that D72A mutant lost its activity but the activity of D71A mutant was not affected (Wang, J. et al., J. Biol. Chem. 277, 46659-46668, 2002).

Enzymatically important residues (Cys104, Arg110 and Asp72) of PRL-1 are arranged the same as they are arranged in VHR. However, homology of neighboring area to the important residues was very low, causing differences in pocket surface and side chain interaction (see FIG. 5 and FIG. 7).

One of the big differences is that amino acid residues in P-loop (Val105-Ala106-Gly107-Leu108-Gly109; SEQ ID NO:8) of PRL-1, wherein numbers of amino acid residues correspond to a full length PRL-1 protein having the amino acid sequence of SEQ ID NO: 6 are hydrophobic, unlike amino acid residues of VHR (Arg125-Glu126-Gly127-Tyr128-Gly129; SEQ ID NO:9), wherein numbers of amino acid residues correspond to a full length VHR protein having the amino acid sequence of SEQ ID NO:13. While hydrophilic side chains of Arg125 and Tyr128 of VHR face outer of active region pocket to form a hydrogen bond with His70 and Ser24, the corresponding residues in PRL-1, Val105 and Ala106, face inside of the pocket, causing hydrophobicity of the pocket surface of PRL-1 (see FIG. 7).

The protruded Met69 side chain in β3-α2 of VHR forms one side of active region pocket, while the corresponding loop of PRL-1 is cut off to form another shape of pocket. Because of the cut of β3-α2 region and another loop around, the active region of PRL-1 has wider but thinner pocket entrance than VHL has. The width of pocket of other phosphatase is less than 6 Å (PTP1B:5.8, VHR:5.0), but the width of pocket of PRL-1 is 8 Å. Such high hydrophilicity and wider pocket entrance of PRL-1 can greatly contribute to the development of a PRL phosphatase specific inhibitor (see FIG. 9).

From the comparison of corresponding sequences based on structure, it was confirmed that PRL-3 has a very similar structure to that of PRL-1 and only 14 out of total 173 residues were nonhomologous residues and the rest are the same (135 residues, 78%) or has a high homology (24 residues, 14%) among them (see FIG. 5). More important finding was that the homologous residues mainly reside on the surface of the molecule containing enzyme active site (see FIGS. 9A and B). Thus, the active site of PRL-3 is very similar to that of PRL-1 and the difference of functions between the PRL proteins is attributed to the difference of structure of the opposite to active site.

However, the similarity of the structures between PRL-1 and PRL-3 supported by the comparison of corresponding sequences has been in controversy since a recent study reported that NMR structure of PRL-3 is much different from active site of PRL-1 (see FIG. 8). Sequences of P-loop and WPD-loop structures are not corresponded to each other. PTP loops were compared between PRL-1 and PRL-3. As a result, the loop was moved nearer to β1 and β2 strands, making active site flat, compared with that of PRL-1. Cys104 of PRL-3 faced outer of a molecule, unlike in PRL-1 and every backbone chain amide nitrogen atoms in major PTP loop of PRL-3 did not face active site, indicating that the NMR structure above might not be a stable active structure. The structure of WPD loop was investigated. Asp72 of PRL-3 was 11.3 Å far from the corresponding position of homologous residue of PRL-1. The changes of location of WPD loop structure is believed to be attributed to the flexibility of loop forming a closed structure through the bond of substrate or substrate-like materials such as sulphuric acid ion in PRL-1.

In variety of surface properties near active site play an important role in recognition of PTP substrate (Salmeen, A. et al., Molecular Cell 6, 1401-1412, 2000; Schumacher M. A. et al., Biochemistry 41, 3009-3017, 2002; Zhou, B. et al., J. Biol. Chem. 276, 6506-6515, 2001).

In PRL-1 structure, secondary phosphate binding region is near active site and patch having positive charge composed of Arg134, Arg137 and Arg 138 is also there (see FIG. 9C). Arg138 is only found in PRL-1, and Arg134 is corresponding to Arg155 of VHR. Arg155 of VHR is covered by loop 22-26 which is not included in PRL-1. The above findings are all involved in substrate specificity of PRL-1. PRL-1 also contains clusters of anionic residues composed of Glu50, Asp 71 and Asp72 (see FIG. 9C). The general electrostatic characteristic of the surface of PRL-1 is much more hydrophobic than that of VHL. The different surface characteristic is an important hall-mark for recognizing tertiary structure of a target protein.

Loop α0-β1 plays an important role in recognition of PTP substrate (Schumacher M. A. et al., Biochemistry 41, 3009-3017. 2002; Song, H. et al., Mol. Cell. 7, 615-626, 2001). In VHR and kinase-associated phosphatase (KAP), substrate is bound by using groove between active site loops which bind loop α0-β1 and a peptide having enlarged loop structure. PRL-1 is deficient in α0 helix, meaning that it does not harbor loop α0-β1, which distinguishes a substrate binding interaction of PRL-1 from that of other PTPs. The surface of active site of PRL-1 is deficient in not only α0 helix and loop α0-β1 but also other projected loops, resulting in almost even active site surface. Such surface characteristic of PRL-1 supports that ATF7 protein, a target protein of PRL-1, is a helical coiled-coil protein, while other PTPs have expanded loop structure. Flat surface structure is essential for helical protein binding. In the meantime, extended loop structure is essential for the binding of a protein having a grooved surface structure. The flat surface structure of PRL-1 can interact with helical protein-tubulins to regulate the growth of spindle fiber (Lowe, J. et al., J. Mol. Biol. 313, 1045-1057, 2001).

The low pKa value and increased reactivity of cysteine make oxidation easy and smooth (Meng, T.-C. et al., Molecular Cell 9, 387-399, 2002). At this time, the primary oxidation of cysteine into sulfenic acid occurs reversibly by thiol reduction, but oxidation into sulfinic acid or sulfonic acid results in the irreversible destruction of enzyme activity.

Recently, mechanisms for the protection of PTP from such oxidative damage have been reported. Cell-cycle dependent CDC25C phosphatase contains catalytic cysteine in which oxidation is induced, and other cysteine forming disulfide bond (Savitsky, P. A. et al., J Biol. Chem. 277, 20535-20540, 2002). In PTP1B, cysteine is linked with amide atom of backbone chain by imino bond (Salmeen, A. et al., Nature 423, 769-773, 2003; van Montfort, R. L. et al., Nature 423, 773-777, 2003). This is a kind of reversible modification, which can protect catalytic cysteine from permanent damage.

The present inventors confirmed that another cysteine resides near catalytic Cys104 of PRL-1, like the case of CDC25. The Cys49 is approximately 5 Å far from Cys104, and no other structure is in-between, suggesting that the two cysteines can be linked each other by disulfide bond without any structural changes (see FIG. 6).

In order to confirm the linkage of the two cysteines by disulfide bond in PRL-1, the present inventors induced hydrogen peroxide ($H_2O_2$) oxidation in purified wild type PRL-1. Reduced or oxidized samples were alkylated by the treatment of iodoacetamide and trypsin, followed by analysis with MALDI mass spectrometer. As a result, a peptide harboring Cys49 and Cys104 alkylated by reduction was found (see Table 2). A peptide containing Cys104 showed a partial alkylation in the regions of Cys98 and Cys99, which is closely related to relative inaccessibility of the above amino acid residue to solvent, in crystal structure. A peak which was the same as that of a disulfide bonded protein harboring Cys49 and Cys104 was found under the condition of oxidation, but a peak which corresponded to reduced cysteine was not detected. Those results indicate that disulfide bond between Cys49 and Cys104 is formed under the condition of oxidation. The reversible disulfide bond plays an important role in protection of PRL-1 from oxidative damage caused during the regulation of oxidation-reduction by PRL-1.

The present inventors also confirmed that PRL-1 protein formed a trimer in crystal structure (see FIG. 3 and FIG. 4). To form the trimer, each monomer overlapped one another by 2,027 Å (25.8% of each whole monomer surface). Contact surface of the trimer has numbers of hydrogen bonds and hydrophilic surface forming van der Waals interaction.

Residues of loop α5-α6 (Asp128, Gln131, Arg134, Gln135 and Arg138) of the first PRL-1 molecule interact with residues of β1 strand (Glu11 and Thr13), loop α1-βb (Lys39 and Tyr40) and α3-β5 (Pro96 and Gly97) of the second molecule. In the center of the trimer, hydrophobic patch containing Tyr14 and Phe132 exists to stabilize the region.

In order to investigate the possibility of forming PRL-1 trimer in a cell, the present inventors performed various biochemical experiments. First, the formation of a trimer was investigated using purified PRL-1 protein used for crystallization. Gel filtration and ultracentrifugation were performed by using 1~2 mg/ml of PRL-1 protein. Although the formation of oligomer was not confirmed, monomer and oligomer were found being dispersed in mix by the mechanical light scattering experiment at higher concentration (~7 mg/ml).

In vivo farnesylated PRL-1 is a simple but clear proof of timer formation (see FIG. 10). The present inventors expressed PRL-1 protein in HEK293 cells and then separated cell membranes to investigate the relation of PRL-1 bias on cell membrane and trimer formation.

PRL-1 structure used herein was either full length protein containing C-terminal farnesylated region or a protein deficient in farnesylated region. As expected, full length PRL-1 protein was farnesylated in a cell, so it dominated in the cell membrane. The interaction of those proteins biased in cell membrane indicated that a trimer was formed in PRL-1.

However, a protein deficient in farnesylated region was not found in cell membrane, and no other polymer was formed, confirmed by cross-linking test. Thus, farnesylated region in PRL-1 protein is significantly involved in the formation of a trimer.

Bias of PRL-1 in cell membrane plays an important role in regulation of cell division (Wang, J. et al, J. Biol. Chem. 277, 46659-46668, 2002). Cell membrane associated trimer formation of PRL-1 affects physiological functions significantly. Farnesylation of protein itself is not an enough mechanism for the protein to migrate to plasma membrane.

Along with prenylation of a monomer, the formation of a polymer between G-proteins forming heterologous trimer and other monomers is essential for the bias in the membrane, according to recent reports (Takida, S. et al., J. Biol. Chem. 278, 17284-17290, 2003). Three farnesyl groups of PRL-1 trimer strongly affect the migration to membrane and stabilize the binding to membrane. The importance of trimer formation in PRL-1 paves the way to the development of a PRL-protein inhibitor by using PRL-1 trimer contacting area.

The present invention also provides a PRL-1 (C104S) protein.

The PRL-1 (C104S) protein is composed of amino acids represented by SEQ. ID. No 1, coming under the range from the $4^{th}$ to $163^{rd}$, and the $104^{th}$ amino acid of active site, cysteine, was mutated into serine to stabilize the protein.

pCRPRL1 vector was constructed for the expression of the PRL-1 (C104S) protein by cloning PRL-1 from human originated cDNA library and then sub-cloning into pET28a. And an *E. Coli* transformant '*E. coli*BL21(DE3)/pCRPRL1' transfected with the vector above was deposited at Korean Collection for Type Cultures (KCTC) of Korea Research Institute of Bioscience and Biotechnology (KRIBB) on Apr. 13, 2004 (Accession No: KCTC 10621BP).

The present invention also provides a method for crystallization of PRL-1 protein.

Particularly, the present invention provides a method for crystallization of PRL-1 protein comprising the following steps:

1) the step of expressing and purifying PRL-1 protein; and
2) the step of optimizing crystal of the protein, expressed and purified in the above step 1), by using a preserving solution containing 10~30% (w/v) PEG 4000 or PEG 8000, 0.05~0.5 M sodium acetate (pH 4.0~6.0), 0.05~1.0 M magnesium sulfate or ammonium sulfate, 3~10% glycerol and 0.5~50 mM DTT.

In the above step 2), the preferable concentrations of each component in the preserving solution are as follows; PEG4000 or PEG 8000 is added preferably by 15~25% (w/v), sodium acetate is added preferably by 0.05~0.2 M, and the preferable pH for sodium acetate is 4.0~5.0. Further, magnesium sulfate or ammonium sulfate is added thereto preferably by 0.05~0.5 M, glycerol is added preferably by 5~8%, and DTT is added preferably by 1~20 mM.

In the preferred embodiment of the present invention, the present inventors separated and purified PRL-1 (C104S) protein produced in transformant *E. coli*BL21(DE3)/pCRPRL1. The protein produced in the present invention by using the expression vector was histidine labeled, which enabled the purification with nickel-affinity chromatography. The labeled histidine was eliminated by treating thrombin thereto, which was then purified again with ion exchange chromatography.

The present invention further provides a screening method for a PRL-1 protein inhibitor comprising the following steps:

1) Mixing PRL-1 protein and a candidate for PRL-1 protein inhibitor;
2) Preparing a crystal of the PRL-1 protein-inhibitor candidate complex by using the method for crystallization of PRL-1 protein of the invention;
3) Analyzing a tertiary structure of the crystal of the complex; and
4) Judging whether or not the candidate blocks PRL-1 active site effectively.

Particularly, the structure of the protein provided by the present invention is available for designing an inhibitor effectively binding to active site of PRL-1 protein. In particular, the conditions for crystallization of PRL-1 protein can be applied to the production of a crystal complex containing a precursor of an inhibitor. Investigation of interaction between the protein and an inhibitor candidate was performed by using software platform containing QUANTA, RASMOL, O, CHAIN, FRODO, INSIGHT, DOCK, MCSS/HOOK, CHARMM, LEAPFROG, CAVEAT(UC Berkley), CAVEAT(MSI), MODELLER, CATALYST, and ISIS, as reported in patent application No. WO 2000/47763.

The present invention also provides a method for the development of a PRL-1 protein inhibitor comprising the following steps:

1) Mixing PRL-1 protein with a candidate for a PRL-1 protein inhibitor;
2) Preparing a crystal of the PRL-1 protein-inhibitor candidate complex by using the method for crystallization of PRL-1 protein of the invention;
3) Analyzing a tertiary structure of the crystal of the complex; and
4) Remodeling the inhibitor above to block active site of PRL-1 effectively.

The structure of a complex of PRL-1 and its inhibitor candidate is very important for designing an effective inhibitor. Since the structure of active site of PRL-1 seems to be almost same as those of PRL-2 and PRL-3, PRL-1 protein crystal can be effectively used for the development of inhibitors for PRL-2 and PRL-3 as well.

In conclusion, the structure of PRL-1 presents detailed information on relation of an enzyme active site and mechanisms of biological regulation. Important residues working as a catalyst in active site are all arranged regularly and have active structures. Cys104 of P-loop and Asp72 of WFPDD-loop are two of the representative examples. PRL-1 structure has a very unique active site pocket and surface property, which provides a clue for the development of an effective PRL-phosphatase inhibitor. From the investigation of crystal structure and biochemical analysis, it was confirmed that PRL-1 forms a trimer attached inside membrane. The formation of membrane linked trimer provides another clue for the development of a tumorigenesis regulator.

In addition, active structure of PRL-1 and its characteristics provide chances of different approaching to the development of a PRL-1 inhibitor, and help us understand specificity of PRL family and biological regulation mechanisms.

DESCRIPTION OF DRAWINGS

The patent or application file contains at least one drawing executed in color. Copies of this patent or patent application publication with color drawing(s) will be provided by the Office upon request and payment of the necessary fee.

BEST MODE

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Expression, Separation and Purification of PRL-1 Protein

A recombinant vector for the expression of PRL-1 protein to be used for the crystallization, pCRPRL1, was constructed by cloning PRL-1 first from human originated fetal brain cDNA library, and then subcloning it again into pET28a.

Figure 11:
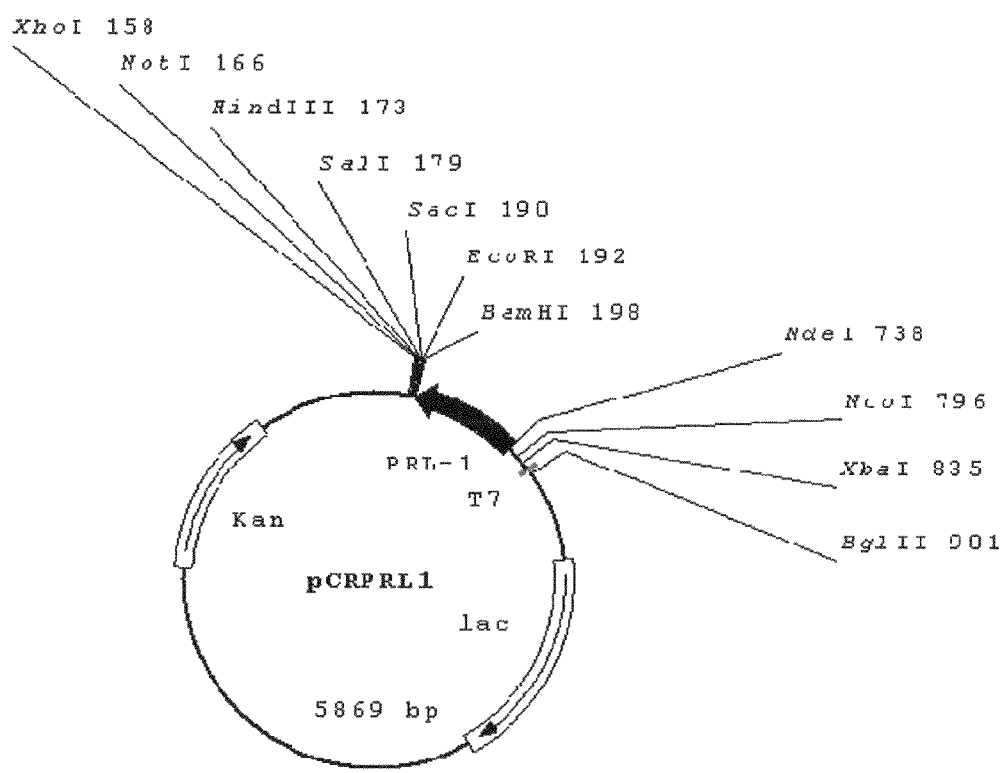
FIG. 11 is a schematic diagram showing the cleavage map of pCRPRL1, an expression vector constructed for the expression of PRL-1 (C104S) protein used for the crystallization of PRL-1 protein of the present invention.

Particularly, PCR was performed to amplify a gene containing amino acids ranging from $4^{th}$ to $163^{rd}$ from cDNA of PRL-1 by using a forward primer represented by SEQ ID No 2 and a backward primer represented by SEQ ID No 3. Then the PCR product was inserted into NdeI-BamHI site of pET28a vector (pCRPRL1C). PCR was performed using a DNA polymerase (Pfu polymerase, Solgent) and the primers as follows; predenaturation at 94° C. for 5 minutes, denaturation at 94° C. for 1 minute, annealing at 55° C. for 1 minute, polymerization at 72° C. for 2 minute, 30 cycles from denaturation to polymerization, and final extension at 72° C. for 10 minutes. In order to secure an excellent crystal, cys104 of the above amino acid sequence of PRL-1 protein was replaced with serine by using Site-directed Quick Change mutagenesis kit (Stratagene) with a forward primer represented by SEQ ID No 4 and a backward primer represented by SEQ ID No 5, and pCRPRL1C as a template. PCR was performed again as follows; predenaturation at 94° C. for 5 minutes, denaturation at 94° C. for 1 minute, annealing at 45° C. for 1 minute, polymerization at 68° C. for 10 minute, 15 cycles from denaturation to polymerization, and final extension at 68° C. for 10 minutes. The PCR product was treated with DpnI enzyme to remove template. Then, the product was transfected into *E. coli* (DH5α). As a result, pCRPRL1 was obtained in which Cys104 of amino acid sequence of PRL-1 was substituted with serine (FIG. 11).

PRL-1 (C104S) protein represented by SEQ. ID. No 1, produced by the vector of the present invention above, has a length ranging from $4^{th}$ amino acid to $163^{rd}$ amino acid, and Cys104, an active site, was substituted with serine for the crystallization. And, farnesylated region of C-terminal was deleted therein. The *E. Coli* transformant (*E. coli* BL21 (DE3)/pCRPRL1) transfected with the above recombinant vector containing sequence of PRL-1 (C104S) was deposited at Korean Collection for Type Cultures (KCTC) of Korea Research Institute of Bioscience and Biotechnology (KRIBB) on Apr. 13, 2004 (Accession No: KCTC 10621BP).

The expression of the *E. Coli* transformant (*E. coli* BL21 (DE3)/PCRPRL1) was induced with 0.1 mM IPTG. Then, the transformant was cultured at 18° C., and the resultant pellets were dissolved in lysis buffer containing 50 mM Tris-HCl (pH 7.5), 200 mM NaCl, 5% glycerol, 0.04% 2-mercaptoethanol and 1 mM PMSF, followed by ultrasonic homogenization. Histidine-labeled PRL-1 protein was purified by nickel-affinity chromatography. The labeled histidine was eliminated with thrombin, which was purified by Q-Sepharose Fast Flow ion exchange chromatography (Pharmacia).

Example 2

Crystallization of PRL-1 Protein

Crystallization was performed by using vapor diffusion method at 18° C. with screening solution on market. Crystallization drops were composed of the protein and reservoir by 1.7 ul respectively, and the drops were adjusted in reservoir containing 25% (w/v) PEG 4000, 0.1 M sodium acetate (pH 4.6) and 0.2 M ammonium sulfate, resulting in a thin plate crystals within a week. The optimized crystal was obtained from the reservoir containing 15% (w/v) PEG4000, 0.1 M sodium acetate (pH 4.6), 0.2 M magnesium sulfate, 7% glycerol and 10 mM DTT.

Monoclinic space group of the crystal produced above was P21, and unit-cell parameters were a=59.29 Å, b=83.76 Å, c=122.18 Å, and β=99.79°.

Example 3

Structure Analysis, Modeling and Refinement of PRL-1 Protein

A crystal produced from selenomethionyl-labeled protein was used to collect MAD (multiple anomalous dispersion) data by 6B Beamline of Pohang Accelerator Laboratory (Postech, Pohang, Korea) (Hendrickson, W. A. et al., Methods Enzymol. 276, 494-523, 1997). Data collected at three wavelengths of peak (λ1), edge (λ2) and remote (λ3) were analyzed by MOSFLM and SCALA program for standardization (Collaborative Computational Project Number 4. The CCP4 suite: programs for protein crystallography Acta Crystallogr. D50, 760-763, 1994).

As a result, asymmetrical unit was confirmed to have 6 monomers of PRL-1 protein. Among 18 selenium sites which were expected to be included in the asymmetrical unit, 12 sites were fixed by SOLVE program (Terwilliger, T. C. et al., Acta Crystallogr. D55, 849-861, 1999). SHARP and DM programs were used respectively for phase enhancement by heavy atom parameter refinement and solvent flattening (Collaborative Computational Project Number 4. The CCP4 suite: programs for protein crystallography Acta Crystallogr. D50, 760-763, 1994; de La Fortelle, E. et al., Methods Enzymol. 276, 472-494, 1997). The experimental map was qualified enough to express most of the protein molecules.

The modeling of the protein was determined by program O (Jones, T. A. et al., Acta Crustallogr. A47, 110-119, 1991) and refinement of the protein was accomplished by program CNS (Brunger, A T. et al., Acta Crustallogr. D54, 905-921, 1998) at the resolution of 99~2.7 λ. 5% of total data was randomly selected for Rfree calculation. Data collected at remote wavelength (λ3) were used for refinement. The refinement process included the refinement of bicameral B factor and the correction of solvent size. NCS limitation was in effect all through the refinement process. Rcryst and Rfree of the final model were 25.6 and 31.2% respectively (Table 1). From stereochemical analysis using program PROCHECK (Laskowski, R. A. et al., J. Appl. Cryst. 26, 283-291, 1993), it was confirmed that 79.2% of refined residues showed predominance in position and no residue in opposite to the structure was found. The final model of structure included the 156$^{th}$ residue in molecules A, B and E; the 8$^{th}$~25$^{th}$ or the 30$^{th}$~156$^{th}$ residues in molecule C; the 8$^{th}$~25$^{th}$ or the 28$^{th}$~50$^{th}$ or the 54$^{th}$~156$^{th}$ residues in molecule D; and the 8$^{th}$~25$^{th}$ or the 28$^{th}$~156$^{th}$ residues in molecule F, and each molecule contains sulfate.

TABLE 1

| Crystal data of PRL-1 protein | | | |
|---|---|---|---|
| | Peak(λ1) | Edge(λ2) | Remote(λ3) |
| A. Statistics of data collection | | | |
| Wavelength (Å) | 0.9792 | 0.9794 | 0.9716 |
| Space group | P21 | | |
| Cell size a, b, c(Å) | 59.29, 84.76, 122.18 | | |
| α, β, γ(°) | 90.00, 99.79, 90.00 | | |
| Maximum resolution (Å) | 2.7 | 2.7 | 2.7 |
| Unique reflection (total) | 30,169(128,838) | 30,188(128,939) | 31,154(135,809) |
| Perfection degree 1(%) | 92.0(95.7) | 92.0(95.7) | 95.2(97.8) |
| Rmerge 2(%) | 7.9(23.5) | 7.7(23.2) | 7.8(23.5) |
| I/σ(I) | 6.9(3.1) | 6.9(3.1) | 7.3(2.9) |
| B. Refinement | | | |
| Resolution range(Å) | | | 99-2.7 |

TABLE 1-continued

| Crystal data of PRL-1 protein | | | |
|---|---|---|---|
| | Peak(λ1) | Edge(λ2) | Remote(λ3) |
| Reflection number | | | 31,124 |
| Atom number (Protein/non-protein) | | | 7,059/30 |
| Rcryst | | | 25.6 |
| Rfree | | | 31.2 |
| R.m.s. deviation | | | |
| Bond length (Å) | | | 0.009 |
| Bond angle(°) | | | 1.5 |
| Error angle(°) | | | 1.1 |
| Diheadral angle(°) | | | 23.1 |

1. The values in brackets (perfection degree and Rmerge) present maximum resolution.
2 Rmerge = Σi | Ii − <I>| Σ|<I>|, wherein, the I means luminous intensity for the measurement of i$^{th}$ of equivalent reflection having h, k and I induces.

Example 4

Mass Spectrometry for Elucidating Disulfide Bond in PRL-1

Figure 1:
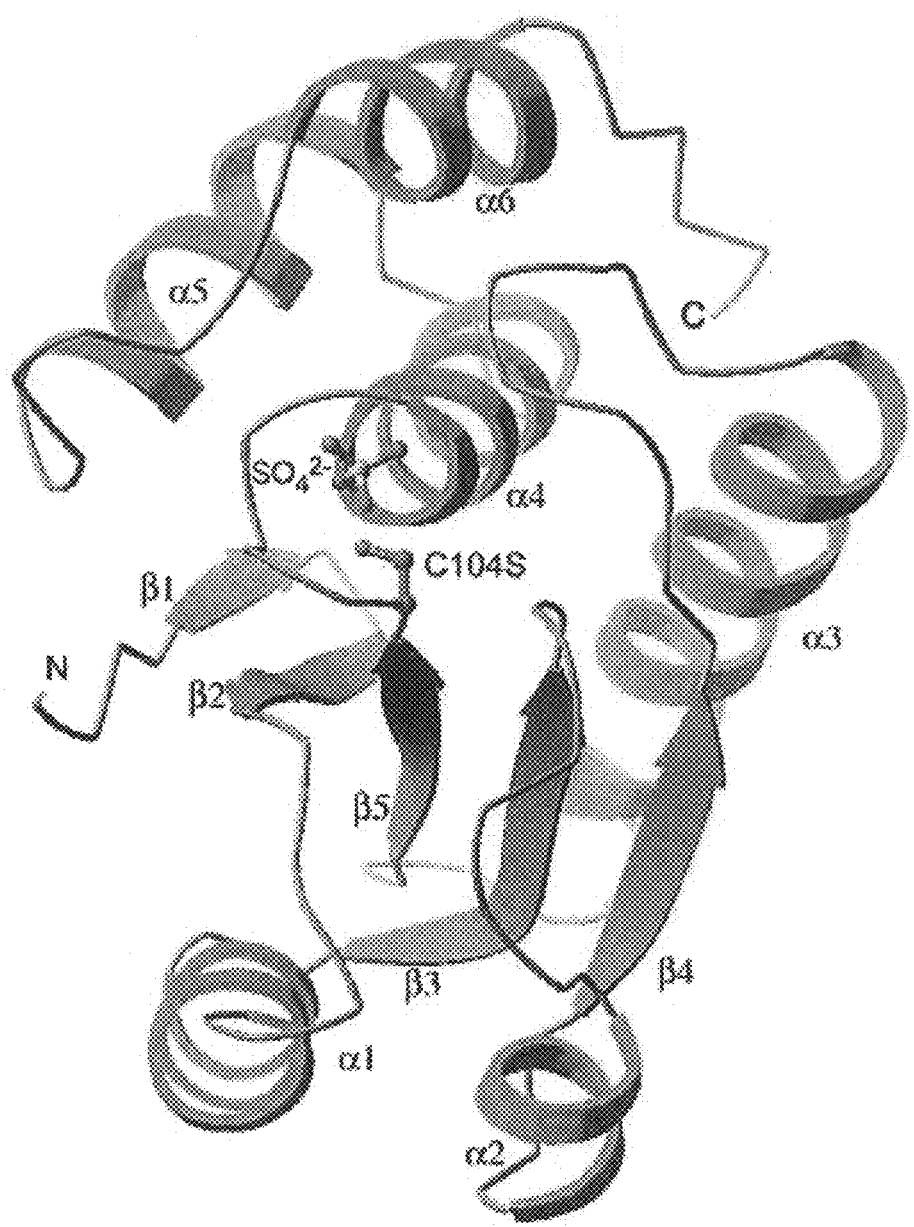
FIG. 1 is a ribbon diagram of PRL-1 protein structure showing the secondary structure (helices: purple, strands: blue, loop: yellow), and the locations of cys104 of active site having serine replaced and fused sulfate ion.
Figure 2:
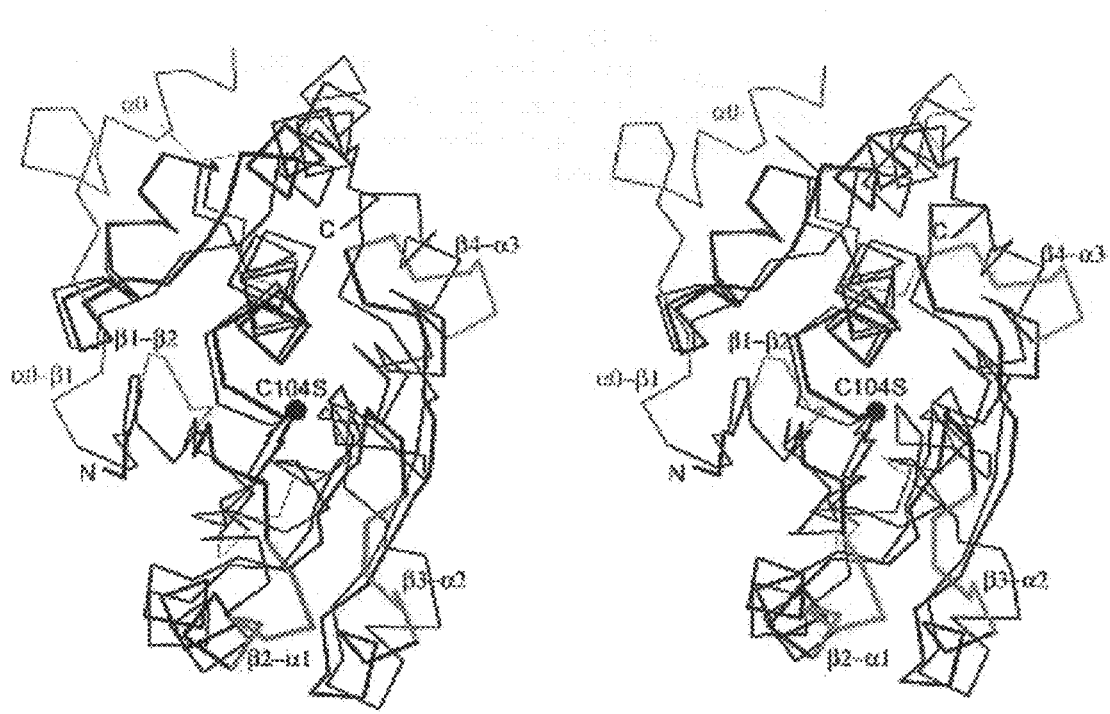
FIG. 2 is a set of schematic diagrams showing the overlapping of VHR structure (thin line) and PRL-1 structure (thick line), precisely, the backbone structure diagram showing non-corresponding region of PRL-1 with VHR (green) and structural factors not found in PRL-1 (red)
Figure 3:
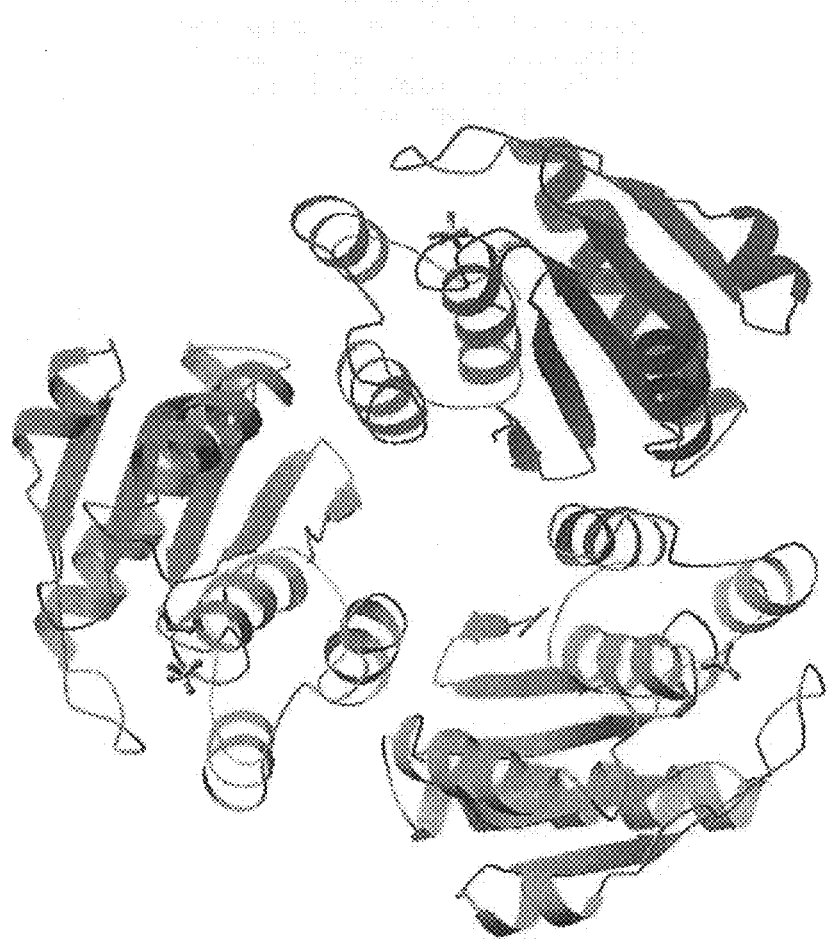
FIG. 3 is a ribbon diagram showing the trimer structure of PRL-1.
Figure 4:
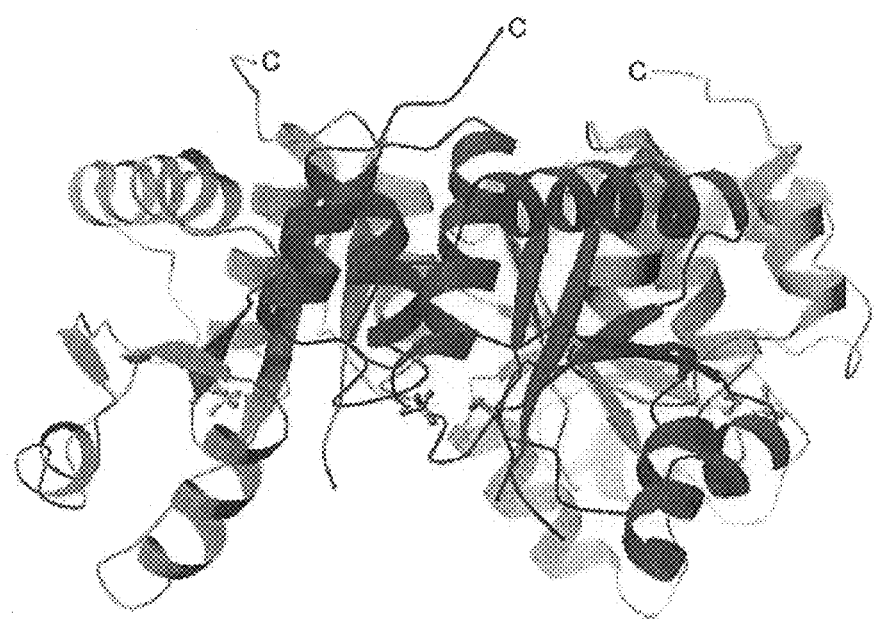
FIG. 4 is a ribbon diagram of trimer structure of PRL-1 showing that C-terminal tails reside in the opposite of active site, facing the same direction.
Figure 5:
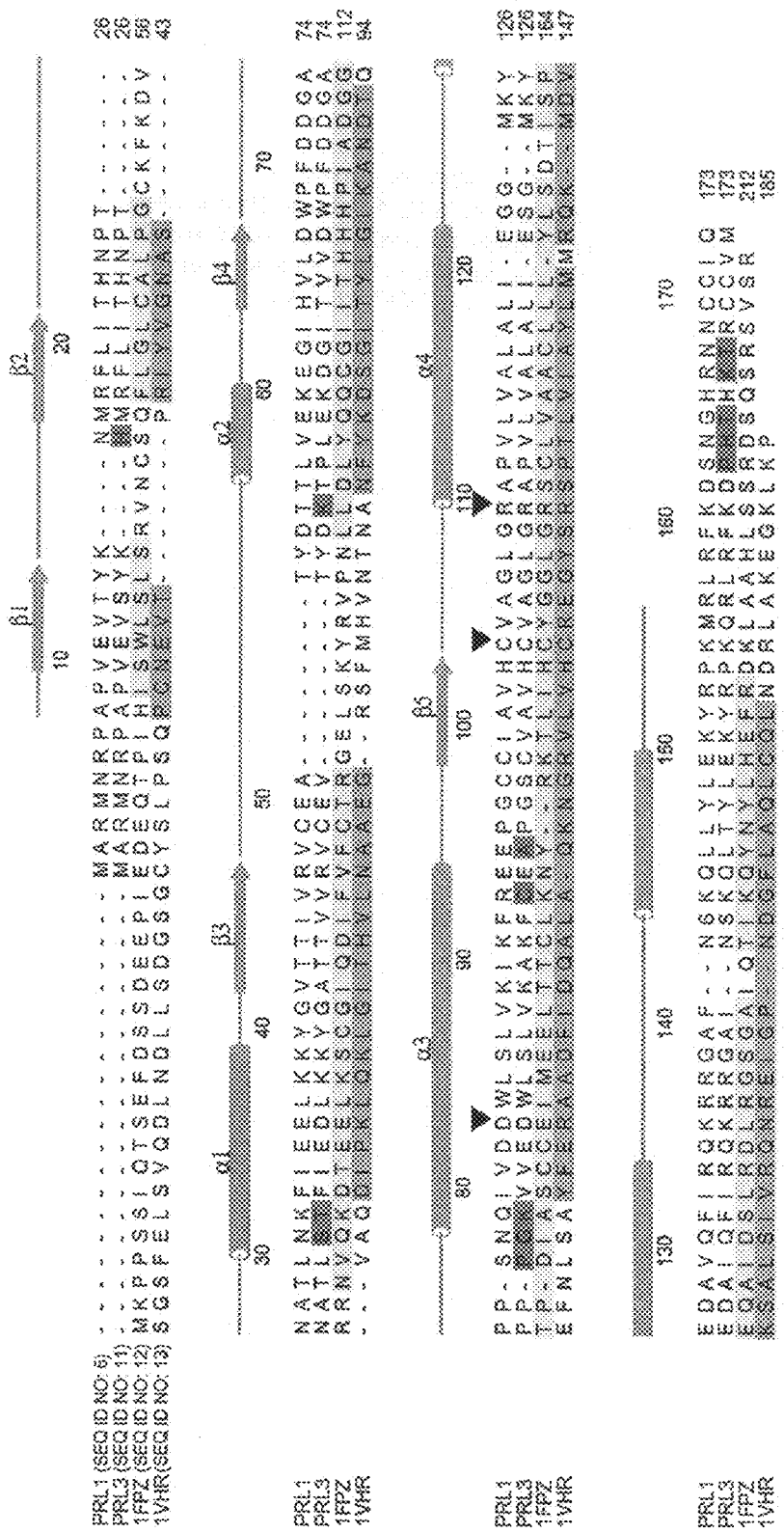
FIG. 5 presents the result of comparison of sequences between PRL-1 (SEQ ID NO:6) and other phosphatases, such as PRL-3(SEQ ID NO:11), KAP (SEQ ID NO:12) and VHR (SEQ ID NO:13)
Figure 6:
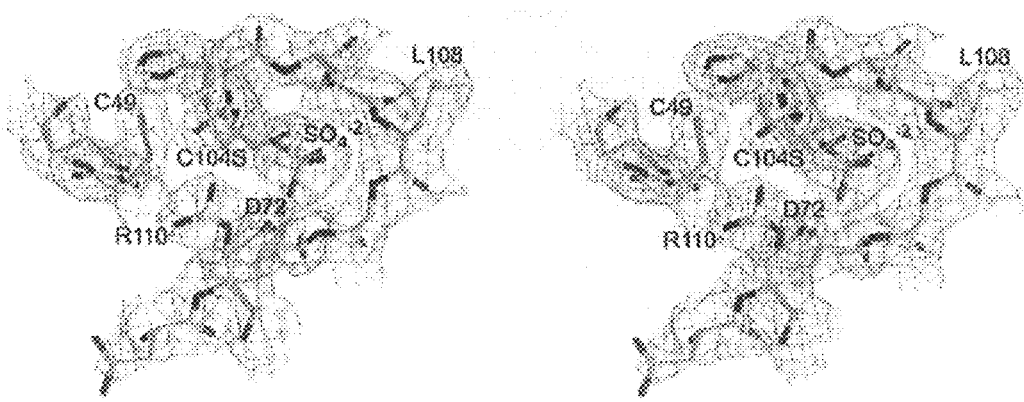
FIG. 6 is a set of schematic diagrams showing the tertiary structure representing electron density map of PRL-1 at 1σ level.
Figure 7:
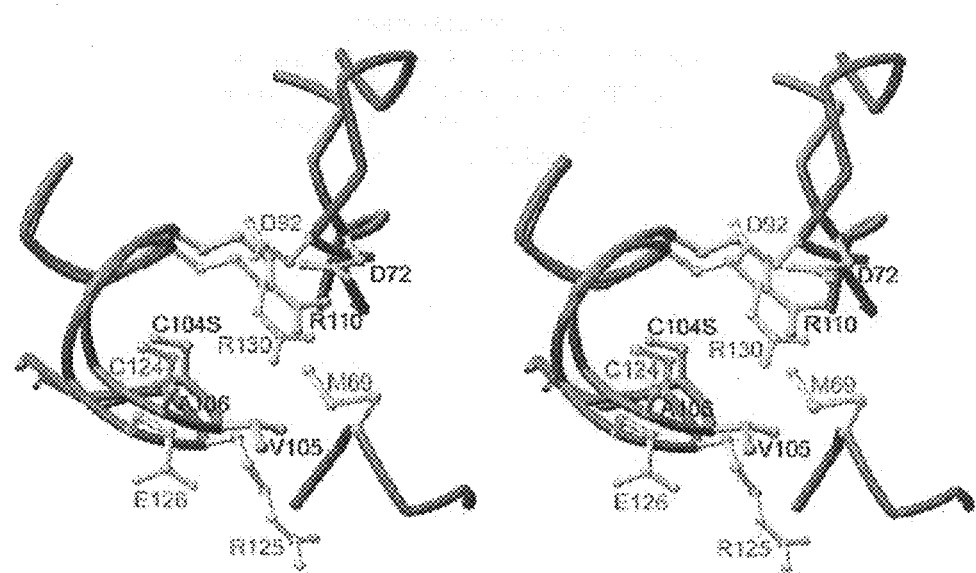
FIG. 7 is a set of schematic diagrams showing the worm model of active sites representing PRL-1 (green) and VHR (red) in which PRL-1 residue is marked by black, VHR residue is marked by red.
Figure 8:
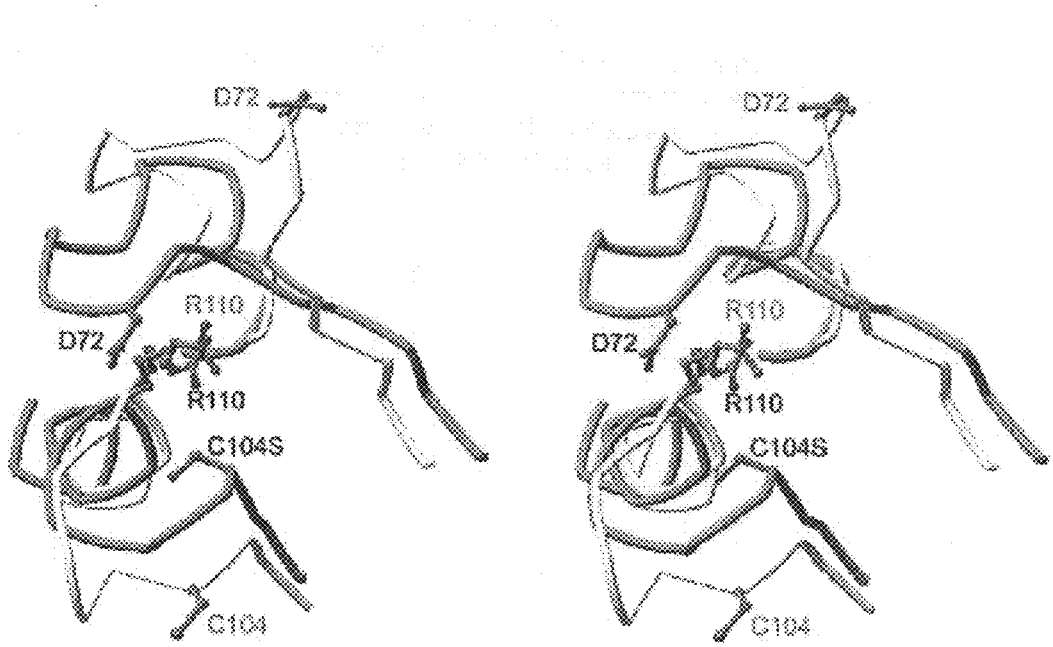
FIG. 8 is a set of schematic diagrams showing the worm model of active sites representing PRL-1 (green) and PRL-3 (red) in which PRL-1 residue is marked by black, PRL-3 residue is marked by red, FIG. 9A (active site) and 9B (opposite of active site) are schematic diagrams showing the tertiary surface structure representing homology between PRL-1 and PRL-3 sequences, investigated by ALSCRIPT program, which is expressed by colors that is, the identical sequences are shown as white, similar sequences are shown as green and different sequences are shown as blue green, measured by overlapping the sequences on the surface map of PRL-1.
Figure 9:
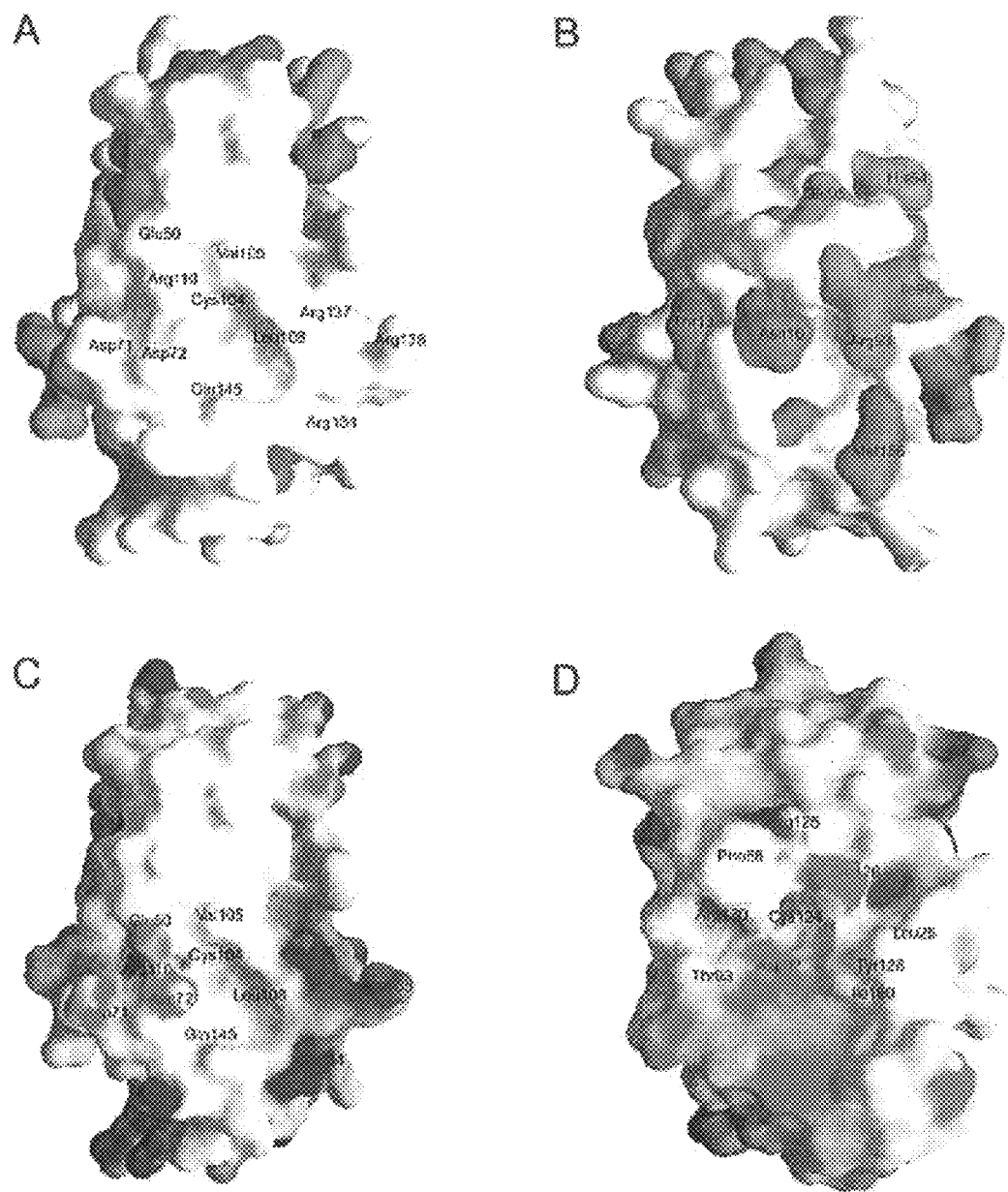
FIGS. 9C and 9D are schematic diagrams showing the tertiary surface structure representing electrostatic potentials of PRL-1 and VHR in which positive potential is marked by blue, negative potential is marked by red.

Another cysteine was found near catalytic Cys104 in the structure of PRL-1. The cysteine (Cys49) was approximately 5 Å far from Cys104, and there was no other structure between them (FIG. 6), indicating that the two cysteines can be linked by disulfide bond without any structural changes. In order to confirm disulfide bond between the two cysteines in PRL-1, the present inventors performed experiment to induce hydrogen peroxide ($H_2O_2$) oxidation in refined wild type PRL-1. Reduced or oxidized samples were treated with iodoacetamide and trypsin to induce alkylation, and then analyzed with a MALDI mass spectrometer.

Particularly, refined protein was put in a buffer solution containing 20 mM Hepes-NaOH (pH 7.0), 0.2 M NaCl and 20 mM DTT for 10 minutes, resulting in reduced PRL-1 (4-163 residues). To prepare oxidized PRL-1, PRL-1 refined in 2 mM DTT was dialyzed in a buffer solution containing 20 mM hepes-NaOH (pH 7.0) and 0.15 M NaCl for overnight. The dialyzed PRL-1 protein was treated with 500 μM $H_2O_2$ (approximately 10 gram-equivalent of PRL-1 protein) for 5 minutes, then 1 g of catalase was added to terminate the oxidation. The reduced and oxidized two protein samples (5 μM) were treated with 20 mM of iodoacetamide in an oxygen-free chamber for alkylation of a free cysteine. 2 μl of 0.5 mg/ml of trypsin was added thereto, followed by digestion at 37° C. for overnight. 2 μl of 10% trifluoroacetic acid was added to terminate the reaction. The digested product was analyzed with Ettan MALDI-TOF mass spectrometer (Amersham Pharmacia, USA) (Table 2).

TABLE 2

| Disulfide bond location of active site | | | | | |
|---|---|---|---|---|---|
| | | | | PRL-1 (4-163) | |
| Peptide | Sequence | Modification | Expected value | Reduced form | Oxidized form |
| 48-60 | VCEATYDTTLVEK | [A | 1528.72 | 1528.72 | — |

TABLE 2-continued

Disulfide bond location of active site

PRL-1 (4-163)

| Peptide | Sequence | Modification | Expected value | Reduced form | Oxidized form |
|---|---|---|---|---|---|
| 94-110 | EEPGCCIAV HCVAGLGR | [A | 1770.81 | 1768.84 | — |
|  |  | 2[A | 1827.83 | 1827.88 | — |
|  |  | 3[A | 1884.85 | 1884.78 | — |
| Cys49-Cys104 | VCEATYDTT LVEK EEPGCCIAV HCVAGLGR | —S—S— +2[A | 3297.52 |  | 3298.20 |

As a result, a peptide including Cys49 and Cys104 alkylated under the condition of reduction was found. A peptide having Cys104 showed partial alkylation in the regions of Cys98 and Cys99, which is closely related to the relative inaccessibility of the amino acid residue to solvent in the crystal structure. A peak showing similarity to a peptide harboring Cys49 and Cys104 linked by disulfide bond was detected under the condition of oxidation, but a peak corresponded to the reduced cysteine was not observed. The above results indicate that Cys49 and Cys104 are linked by disulfide bond under the condition of oxidation. The reversible disulfide bond plays an important role in protection of PRL-1 protein from getting oxidative damage generated during its regulation of oxidation and reduction.

Example 5

Separation at the Undercellular Level and Chemical Cross-Linking Experiment to Elucidate Bias of PRL-1 in Cell Membrane and Trimer Formation The present inventors induced the expression of PRL-1 protein in HEK293 cells and then separated cell membranes to investigate the association of bias of PRL-1 in cell membrane with the formation of a trimer.

First, full length (1~173 residues) and C-terminal lacking (1~163 residues) PRL-1 DNAs were inserted into NheI/BamHI site of pcDNA3.1/Zeo(+) (Invitrogen) harboring FLAG tail sequence at N-terminal, which is known as a mammalian expression plasmid. HEK293 cells were cultured in medium (Dulbecco's Eagle's medium, Life Technologies, Inc) supplemented with 10% fetal bovine serum and antibiotics.

Figure 10:
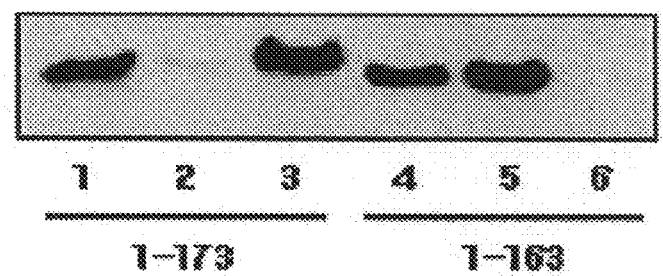
FIG. 10A is an electrophoresis photograph showing the intracellular bias of full length PRL-1 (lane 1~3) and PRL-1 deficient in C-terminal (lane 3~6), Lane 1 and Lane 3: Cell lysate,
Lane 2 and Lane 4: S100, Lane 3 and Lane 6: P100
FIG. 10B is an electrophoresis photograph showing the cross-linking of intracellular membrane fraction (p100) in full length PRL-1, Lane 1: 0% glutaraldehyde,
Lane 2: 0.01% glutaraldehyde,
Lane 3: 0.02% glutaraldehyde,
Lane 4: 0.04% glutaraldehyde
Figure 10:
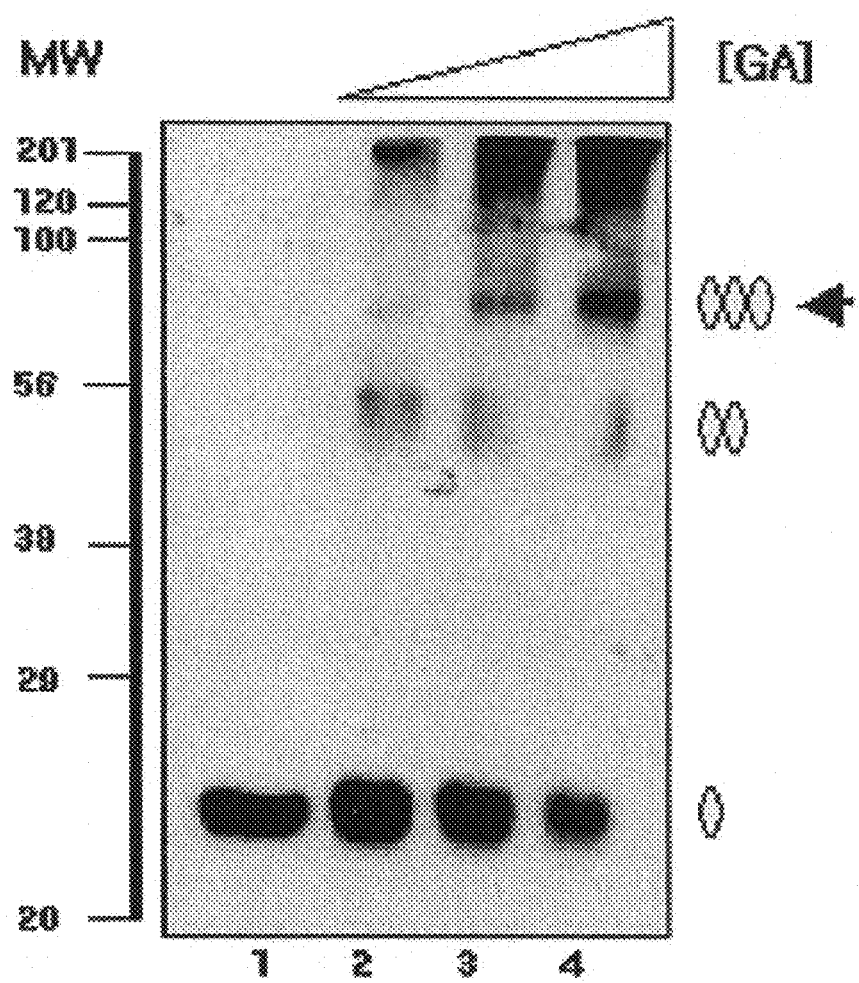

The mentioned mammalian expression vector was introduced into HEK293 cells by LipofectAMINE method (Life Technologies Inc), and temporarily transfected cells were washed with ice-cooled buffer solution A containing 25 mM Hepes-NaOH (pH 7.0), 250 mM sucrose, 5 mM EDTA, 2 mM DTT, 1 mM PMSF and protease inhibitor cocktail, followed by centrifugation for 5 minutes. The cell pellet was dissolved again in 200 µl of buffer solution A, and then crushed 35 times using homogenizer. The non-crushed cells were removed by centrifugation at 20,000 g for 10 seconds. The supernatant was centrifuged at 100,000 g at 4° C. for one hour. The resultant supernatant (S100) and corpuscular fraction (P100, membrane fraction) were used for cross-linking experiment. Cross-linking of corpuscular fraction (P100) was accomplished by glutaraldehyde reaction. Corpuscular fraction (P100) in buffer solution A was treated with 0.01, 0.02 or 0.04% glutaraldehyde at 25° C. for 30 minutes, and the reaction was terminated by adding 1.0 M Tris-HCl (pH 7.5). The reaction result was confirmed by SDS-PAGE. The protein was confirmed by immunoblotting with anti-FLAG M1 monoclonal antibody (Sigma-Aldrich), and the protein band was confirmed by chemical luminescence detection system (PIERCE) after being reacted with peroxidase binding anti-mouse secondary antibody (FIG. 10).

PRL-1 structures used for the experiments herein were both full length and farnesylated region defected proteins. The full length PRL-1 protein was farnesylated, so that it showed predominance in cell membrane, as expected, and mutual coupling among them biased in the membrane suggested the formation of a trimer in PRL-1.

However, shorter PRL-1 protein deficient in farnesylated region was not observed in cell membrane. Cross-linking experiment also confirmed that other polymers were not formed, indicating that farnesylated region in PRL-1 protein is significantly involved in the formation of a trimer in membrane.

INDUSTRIAL APPLICABILITY

As explained hereinbefore, the present invention confirmed that tertiary active structure of PRL-1 protein by providing a method for crystallization in which human originated PRL-1 protein is mass-expressed in *E. Coli* transformant and then refined and crystals prepared thereby. PRL-1 structure contains detailed information on relation of enzyme active site and biological regulation mechanisms, and has a unique active site pocket and surface property, which provides an important clue for the development of a PRL-protein specific inhibitor. The formation of trimer attached on membrane, proved by the crystal structure of the present invention and biochemical analysis as well, provides another possibility of development of an agent or an inhibitor regulating the carcinogenic activity of PRL-1.

[Sequence List Text]

SEQ. ID. No 1 is an amino acid sequence ranging from the $4^{th}$ to the $163^{rd}$ amino acid of PRL-1 protein (C104S).

SEQ. ID. No 2 and No. 3 are a forward primer and a backward primer, respectively, to amplify a gene containing amino acids ranging from the $4^{th}$ to the $163^{rd}$ from cDNA of PRL-1.

SEQ. ID. No 4 and No. 5 are a forward primer and a backward primer, respectively, to replace Cys104 of amino acid sequences of PRL-1 protein into serine.

SEQ ID NO: 6 is the amino acid sequence of full length human PRL-1 protein.

SEQ ID NO: 7 is the amino acid sequence of P-loop of PRL-1 protein

SEQ ID NO: 8 is the amino acid sequence of five amino acid residues in the P-loop.

SEQ ID NO: 9 is the amino acid sequence of VHR domain of PRL-1 protein.

SEQ ID NO: 10 is the amino acid sequence of WFPDD loop of PRL-1 protein.

SEQ ID NOs: 11 to 13 are the amino acid sequences of human PRL-3 protein, CAP phosphatase and VHR phosphatase, respectively.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A crystal of phosphatase of regenerating liver-1 (PRL-1) protein, wherein the PRL-1 protein comprises SEQ ID NO:1 and the crystal has monoclinic space group of P2$_1$ and unit-cell parameters of a=59.29 Å, b=83.76 Å, c=122.18 Å and β=99.79°.

2. The crystal of PRL-1 protein as set forth in claim 1, wherein 6 PRL-1 protein molecules are included in an asymmetric unit.

3. The crystal of PRL-1 protein as set forth in claim 1, wherein the PRL-1 protein has a tertiary structure having 5 strands of β-sheet (β1-β5) in the center surrounded by 6 α-helices (α1-α6), in which one side of the β-sheet is covered with α1 and α2 α-helices and the other side of the β-sheet is covered with α3-α6 α-helices.

4. The crystal of PRL-1 protein as set forth in claim 3, wherein the α1 α-helix is composed of $30^{th}$-$39^{th}$ amino acid residues; α2 α-helix is composed of $56^{th}$-$60^{th}$ amino acid residues; α3 α-helix is composed of $78^{th}$-$94^{th}$ amino acid residues; α4 α-helix is composed of $110^{th}$-$121^{st}$ amino acid residues; α6 α-helix is composed of $143^{rd}$-$150^{th}$ amino acid residues; β1 β-sheet is composed of $17^{th}$-$21^{st}$ amino acid residues; β2 β-sheet is composed of $42^{nd}$-$47^{th}$ amino acid residues; β3 β-sheet is composed of $64^{th}$-$67^{th}$ amino acid residues; β4 β-sheet is composed of $64^{th}$-$67^{th}$ amino acid residues; and, β5 β-sheet is composed of $99^{th}$-$103^{rd}$ amino acid residues, wherein numbers of amino acid residues correspond to a full length PRL-1 protein having the amino acid sequence of SEQ ID NO: 6.

5. The crystal of PRL-1 protein as set forth in claim 1, wherein the PRL-1 protein contains an active site containing a P-loop having the amino acid sequence of SEQ ID NO: 7 (His103-Cys104-(X)$_5$-Arg110) in the center of the protein, a WFPDD loop (SEQ ID NO: 10) in-between $68^{th}$-$72^{nd}$ amino acid residues, a cationic patch of Arg134, Arg137 and Arg138 on the surface, and an anionic cluster of Glu50, Asp71 and Asp7 on the surface, wherein numbers of amino acid residues correspond to a full length PRL-1 protein having the amino acid sequence of SEQ ID NO: 6.

6. The crystal of PRL-1 protein as set forth in claim 5, wherein the active site contains hydrophobic residues of Val105-Ala106- Gly107-Leu108-Gly109 (SEQ ID NO: 8) and a pocket having a wide entrance of 8 Å, wherein numbers of amino acid residues correspond to a full length PRL-1 protein having the amino acid sequence of SEQ ID NO: 6.

7. The crystal of PRL-1 protein as set forth in claim 5, wherein the Cys104 of the active site forms a reversible disulfide bond with Cys49, wherein numbers of amino acid residues correspond to a full length PRL-1 protein having the amino acid sequence of SEQ ID NO: 6.

8. The crystal of PRL-1 protein as set forth in claim 1, wherein the crystal has a tertiary structure in which PRL-1 molecules are in an asymmetric unit, and 3 of the PRL-1 molecules form a trimer by triple symmetrical combination.

* * * * *

SEQUENCE LISTING

<160> NUMBER OF SEQ ID NOS: 13

<210> SEQ ID NO 1
<211> LENGTH: 160
<212> TYPE: PRT
<213> ORGANISM: Homo sapiens

<400> SEQUENCE: 1

Met Asn Arg Pro Ala Pro Val Glu Val Thr Tyr Lys Asn Met Arg Phe
1               5                   10                  15

Leu Ile Thr His Asn Pro Thr Asn Ala Thr Leu Asn Lys Phe Ile Glu
            20                  25                  30

Glu Leu Lys Lys Tyr Gly Val Thr Thr Ile Val Arg Val Cys Glu Ala
        35                  40                  45

Thr Tyr Asp Thr Thr Leu Val Glu Lys Glu Gly Ile His Val Leu Asp
    50                  55                  60

Trp Pro Phe Asp Asp Gly Ala Pro Pro Ser Asn Gln Ile Val Asp Asp
65                  70                  75                  80

Trp Leu Ser Leu Val Lys Ile Lys Phe Arg Glu Glu Pro Gly Cys Cys
                85                  90                  95

Ile Ala Val His Ser Val Ala Gly Leu Gly Arg Ala Pro Val Leu Val
            100                 105                 110

Ala Leu Ala Leu Ile Glu Gly Gly Met Lys Tyr Glu Asp Ala Val Gln
        115                 120                 125

Phe Ile Arg Gln Lys Arg Arg Gly Ala Phe Asn Ser Lys Gln Leu Leu
    130                 135                 140

Tyr Leu Glu Lys Tyr Arg Pro Lys Met Arg Leu Arg Phe Lys Asp Ser
145                 150                 155                 160

<210> SEQ ID NO 2
<211> LENGTH: 33
<212> TYPE: DNA
<213> ORGANISM: Artificial Sequence
<220> FEATURE:
<223> OTHER INFORMATION: Synthetic

<400> SEQUENCE: 2
gcggctcata tgaaccgccc agctcctgtg gaa                              33

<210> SEQ ID NO 3
<211> LENGTH: 36
<212> TYPE: DNA
<213> ORGANISM: Artificial Sequence
<220> FEATURE:
<223> OTHER INFORMATION: Synthetic

<400> SEQUENCE: 3
gcgggatcct caggaatctt tgaaacgcag ccgcat                           36

<210> SEQ ID NO 4
<211> LENGTH: 33
<212> TYPE: DNA
<213> ORGANISM: Artificial Sequence
<220> FEATURE:
<223> OTHER INFORMATION: Synthetic

<400> SEQUENCE: 4
tgtattgctg ttcatagcgt tgcaggcctt ggg                              33

<210> SEQ ID NO 5

```
<211> LENGTH: 33
<212> TYPE: DNA
<213> ORGANISM: Artificial Sequence
<220> FEATURE:
<223> OTHER INFORMATION: Synthetic

<400> SEQUENCE: 5
cccaaggcct gcaacgctat gaacagcaat aca                                    33

<210> SEQ ID NO 6
<211> LENGTH: 173
<212> TYPE: PRT
<213> ORGANISM: Homo sapiens

<400> SEQUENCE: 6
```

Met Ala Arg Met Asn Arg Pro Ala Pro Val Glu Val Thr Tyr Lys Asn
1               5                   10                  15

Met Arg Phe Leu Ile Thr His Asn Pro Thr Asn Ala Thr Leu Asn Lys
            20                  25                  30

Phe Ile Glu Glu Leu Lys Lys Tyr Gly Val Thr Thr Ile Val Arg Val
        35                  40                  45

Cys Glu Ala Thr Tyr Asp Thr Thr Leu Val Glu Lys Glu Gly Ile His
    50                  55                  60

Val Leu Asp Trp Pro Phe Asp Asp Gly Ala Pro Pro Ser Asn Gln Ile
65                  70                  75                  80

Val Asp Asp Trp Leu Ser Leu Val Lys Ile Lys Phe Arg Glu Glu Pro
                85                  90                  95

Gly Cys Cys Ile Ala Val His Cys Val Ala Gly Leu Gly Arg Ala Pro
            100                 105                 110

Val Leu Val Ala Leu Ala Leu Ile Glu Gly Gly Met Lys Tyr Glu Asp
        115                 120                 125

Ala Val Gln Phe Ile Arg Gln Lys Arg Arg Gly Ala Phe Asn Ser Lys
    130                 135                 140

Gln Leu Leu Tyr Leu Glu Lys Tyr Arg Pro Lys Met Arg Leu Arg Phe
145                 150                 155                 160

Lys Asp Ser Asn Gly His Arg Asn Asn Cys Cys Ile Gln
                165                 170

```
<210> SEQ ID NO 7
<211> LENGTH: 8
<212> TYPE: PRT
<213> ORGANISM: Artificial Sequence
<220> FEATURE:
<223> OTHER INFORMATION: P-loop of PRL-1
<220> FEATURE:
<221> NAME/KEY: misc_feature
<222> LOCATION: (3)..(7)
<223> OTHER INFORMATION: Xaa can be any naturally occurring amino acid

<400> SEQUENCE: 7
```

His Cys Xaa Xaa Xaa Xaa Xaa Arg
1               5

```
<210> SEQ ID NO 8
<211> LENGTH: 5
<212> TYPE: PRT
<213> ORGANISM: Artificial Sequence
<220> FEATURE:
<223> OTHER INFORMATION: 105 to 109 amino acid of PRL-1

<400> SEQUENCE: 8
```

Val Ala Gly Leu Gly
1               5

-continued

<210> SEQ ID NO 9
<211> LENGTH: 5
<212> TYPE: PRT
<213> ORGANISM: Artificial Sequence
<220> FEATURE:
<223> OTHER INFORMATION: VHR of PRL-1

<400> SEQUENCE: 9

Arg Glu Gly Tyr Gly
1               5

<210> SEQ ID NO 10
<211> LENGTH: 5
<212> TYPE: PRT
<213> ORGANISM: Artificial Sequence
<220> FEATURE:
<223> OTHER INFORMATION: WFPDD loop of PRL-1

<400> SEQUENCE: 10

Trp Phe Pro Asp Asp
1               5

<210> SEQ ID NO 11
<211> LENGTH: 173
<212> TYPE: PRT
<213> ORGANISM: Homo sapiens

<400> SEQUENCE: 11

Met Ala Arg Met Asn Arg Pro Ala Pro Val Glu Val Ser Tyr Lys His
1               5                   10                  15

Met Arg Phe Leu Ile Thr His Asn Pro Thr Asn Ala Thr Leu Ser Thr
            20                  25                  30

Phe Ile Glu Asp Leu Lys Lys Tyr Gly Ala Thr Thr Val Val Arg Val
        35                  40                  45

Cys Glu Val Thr Tyr Asp Lys Thr Pro Leu Glu Lys Asp Gly Ile Thr
    50                  55                  60

Val Val Asp Trp Pro Phe Asp Asp Gly Ala Pro Pro Pro Gly Lys Val
65                  70                  75                  80

Val Glu Asp Trp Leu Ser Leu Val Lys Ala Lys Phe Cys Glu Ala Pro
                85                  90                  95

Gly Ser Cys Val Ala Val His Cys Val Ala Gly Leu Gly Arg Ala Pro
            100                 105                 110

Val Leu Val Ala Leu Ala Leu Ile Glu Ser Gly Met Lys Tyr Glu Asp
        115                 120                 125

Ala Ile Gln Phe Ile Arg Gln Lys Arg Arg Gly Ala Ile Asn Ser Lys
    130                 135                 140

Gln Leu Thr Tyr Leu Glu Lys Tyr Arg Pro Lys Gln Arg Leu Arg Phe
145                 150                 155                 160

Lys Asp Pro His Thr His Lys Thr Arg Cys Cys Val Met
                165                 170

<210> SEQ ID NO 12
<211> LENGTH: 212
<212> TYPE: PRT
<213> ORGANISM: Homo sapiens

<400> SEQUENCE: 12

Met Lys Pro Pro Ser Ser Ile Gln Thr Ser Glu Phe Asp Ser Ser Asp
1               5                   10                  15

Glu Glu Pro Ile Glu Asp Glu Gln Thr Pro Ile His Ile Ser Trp Leu 20                  25                  30

Ser Leu Ser Arg Val Asn Cys Ser Gln Phe Leu Gly Leu Cys Ala Leu
                35                  40                  45

Pro Gly Cys Lys Phe Lys Asp Val Arg Arg Asn Val Gln Lys Asp Thr
            50                  55                  60

Glu Glu Leu Lys Ser Cys Gly Ile Gln Asp Ile Phe Val Phe Cys Thr
65                  70                  75                  80

Arg Gly Glu Leu Ser Lys Tyr Arg Val Pro Asn Leu Leu Asp Leu Tyr
                85                  90                  95

Gln Gln Cys Gly Ile Ile Thr His His His Pro Ile Ala Asp Gly Gly
            100                 105                 110

Thr Pro Asp Ile Ala Ser Cys Cys Glu Ile Met Glu Glu Leu Thr Thr
        115                 120                 125

Cys Leu Lys Asn Tyr Arg Lys Thr Leu Ile His Cys Tyr Gly Gly Leu
    130                 135                 140

Gly Arg Ser Cys Leu Val Ala Ala Cys Leu Leu Tyr Leu Ser Asp
145                 150                 155                 160

Thr Ile Ser Pro Glu Gln Ala Ile Asp Ser Leu Arg Asp Leu Arg Gly
                165                 170                 175

Ser Gly Ala Ile Gln Thr Ile Lys Gln Tyr Asn Tyr Leu His Glu Phe
            180                 185                 190

Arg Asp Lys Leu Ala Ala His Leu Ser Ser Arg Asp Ser Gln Ser Arg
        195                 200                 205

Ser Val Ser Arg
    210

<210> SEQ ID NO 13
<211> LENGTH: 184
<212> TYPE: PRT
<213> ORGANISM: Homo sapiens

<400> SEQUENCE: 13

Ser Gly Ser Phe Glu Leu Ser Val Gln Asp Leu Asn Asp Leu Leu Ser
1               5                   10                  15

Asp Gly Ser Gly Cys Tyr Ser Leu Pro Ser Gln Pro Cys Asn Glu Val
            20                  25                  30

Thr Pro Arg Ile Tyr Val Gly Asn Ala Ser Val Ala Gln Asp Ile Pro
        35                  40                  45

Lys Leu Gln Lys Leu Gly Ile Thr His Val Leu Asn Ala Ala Glu Gly
    50                  55                  60

Arg Ser Phe Met His Val Asn Thr Asn Ala Asn Phe Tyr Lys Asp Ser
65                  70                  75                  80

Gly Ile Thr Tyr Leu Gly Ile Lys Ala Asn Asp Thr Gln Glu Phe Asn
                85                  90                  95

Leu Ser Ala Tyr Phe Glu Arg Ala Ala Asp Phe Ile Asp Gln Ala Leu
            100                 105                 110

Ala Gln Lys Asn Gly Arg Val Leu Val His Cys Arg Glu Gly Tyr Ser
        115                 120                 125

Arg Ser Pro Thr Leu Val Ile Ala Tyr Leu Met Met Arg Gln Lys Met
    130                 135                 140

Asp Val Lys Ser Ala Leu Ser Ile Val Arg Gln Asn Arg Glu Ile Gly
145                 150                 155                 160

```
Pro Asn Asp Gly Phe Leu Ala Gln Leu Cys Gln Leu Asn Asp Arg Leu
            165                 170                 175

Ala Lys Glu Gly Lys Leu Lys Pro
            180
```